United States Patent [19]

Hori et al.

[11] Patent Number: 5,452,601
[45] Date of Patent: Sep. 26, 1995

[54] METHOD FOR SIMULTANEOUS DETERMINATION OF THERMAL CONDUCTIVITY AND KINEMATIC VISCOSITY

[75] Inventors: Tomoshige Hori, Kitamoto; Kensuke Itoh, Kodaira, both of Japan

[73] Assignee: Snow Brand Milk Products Co., Ltd., Hokkaido, Japan

[21] Appl. No.: 210,990

[22] Filed: Mar. 22, 1994

[30] Foreign Application Priority Data

Mar. 26, 1993 [JP] Japan ................................. 5-067891

[51] Int. Cl.$^6$ ............................ G01N 11/00; G01N 25/18
[52] U.S. Cl. ........................... 73/54.42; 374/15; 374/44; 374/45
[58] Field of Search ................. 73/54.42, 54.02, 73/54.43, 61.46; 374/10, 11, 15, 16, 29, 44, 45, 112

[56] References Cited

U.S. PATENT DOCUMENTS

| | | | |
|---|---|---|---|
| 4,578,988 | 4/1986 | Hori et al. | 73/54.01 |
| 4,947,678 | 8/1990 | Hori et al. | 73/54.42 |
| 4,971,451 | 11/1990 | Hori et al. | 374/16 |
| 4,995,731 | 2/1991 | Hori et al. | 374/44 X |
| 5,014,553 | 5/1991 | Hori et al. | 73/295 |
| 5,017,875 | 5/1991 | Hori et al. | 73/54.42 X |
| 5,044,764 | 9/1991 | Aoki et al. | 374/16 |
| 5,341,672 | 8/1994 | Kawanami et al. | 73/64.54 |

*Primary Examiner*—Hezron E. Williams
*Assistant Examiner*—Michael J. Brock
*Attorney, Agent, or Firm*—Griffin, Butler, Whisenhunt & Kurtossy

[57] ABSTRACT

A heating sensor capable of generating heat and measuring its own temperature is placed in a fluid and a thermometric sensor is placed in the fluid and inside a temperature boundary layer formed around the heating sensor upon heat generation therefrom. A temperature of the heating sensor and a temperature of the fluid are measured. A relationship between thermal conductivity of the fluid and a differential value between the temperature of the heating sensor and the temperature of the fluid is used to determine the thermal conductivity of the fluid. Then, the heating value of the heating sensor is adjustably increased so that the thermometric sensor is positioned outside the temperature boundary layer. A temperature of the heating sensor and the temperature of the fluid are measured. The relationship between kinematic viscosity of the fluid and a differential value between the temperature of the heating sensor and the temperature of the fluid is used to determine the kinematic viscosity of the fluid. Alternatively, a single heating sensor and a pair of the thermometric sensors are used, where one of the thermometric sensors is placed outside the temperature boundary layer, and the other thermometric sensor is placed inside the temperature boundary layer, or a pair of the heating sensors is used with a single thermometric sensor placed outside the temperature boundary layer formed around one of the heating sensors and inside the temperature boundary layer formed around the other heating sensor.

3 Claims, 3 Drawing Sheets

METHOD FOR SIMULTANEOUS DETERMINATION OF THERMAL CONDUCTIVITY AND KINEMATIC VISCOSITY

The present invention relates to a method for the simultaneous determination of thermal conductivity and kinematic viscosity of a fluid using a sensor which is capable of generating heat and measuring its own temperature.

BACKGROUND OF THE INVENTION

In general, the measurement of thermal conductivity and kinematic viscosity is essential to industrial process management for handling general fluids. It is well known to use a sensor which is capable of generating heat and measuring its own temperature, such that temperatures of the sensor itself and the temperature of the fluid to be monitored are measured. Thus, for example state of a fluid is determined on the basis of a characteristic kinematic viscosity value, defined as a function of a differential temperature of the sensor and fluid.

Such thermal methods for measuring the change in physical properties of a fluid are classified into two general methods, i.e. the steady-state and the unsteady-state methods. The unsteady-state method is based upon the temperature of the heating sensor, or a differential temperature between the heating sensor and the fluid, increasing with passage of time immediately after the sensor initiates the generation of heat. The so-called unsteady-state hot wire method, usually used to measure thermal conductivity of fluid, is one example of this unsteady-state method. On the other hand, the so-called steady-state method is based upon the phenomenon that, after a certain period of such heating of the sensor in the unsteady-state, a temperature of the heating sensor, or the differential temperature between the heating sensor and the fluid, becomes constant. It should be understood that, in response to any change in the physical properties of the fluid, such as viscosity, occurring in this steady state, the temperature of the heating sensor will change to a different level but will again stabilize at a constant temperature.

In the prior art, for example, the steady-state method is used to obtain values of various physical properties of a fluid on the basis of the respective temperatures, or to determine the state of a fluid from correlations between a change in temperature and a change in viscosity or other physical properties, as disclosed by the following documents:

A. Japanese Patent Publication No. 76702/1991 entitled "Method for Measurement of Change in Physical Properties of Fluid or Semisolid Substance" discloses a method for non-destructive measurement of a change in physical properties of a fluid comprising the steps of placing a metallic thin wire in the fluid, regulating the electric current applied to the metallic thin wire so that the difference between the temperature of the metallic thin wire and the temperature of the fluid may be maintained constant, and calculating the thermal conductivity of the fluid from the value of the electric current.

B. Japanese Patent Application Disclosure No. 185146/1987 entitled "Method for Fluid State Determination" discloses a method for determining the state of a fluid comprising the steps of placing a sensor in thermal contact with a fluid, measuring the temperature of the sensor itself and the temperature of the fluid, and intermittently or continuously measuring the difference between these temperatures.

For these techniques of the prior art, the temperature measured by the heating sensor is the most important value to be determined, and it is also essential to previously know the particular construction of the sensor, as well as the thermal characteristic of the sensor, or a particular correlation between the measured temperature and physical properties of the fluid.

The above-noted prior art "A" is the basic method for measuring the change in physical properties of a fluid utilizing the hot wire method and is exclusively used to determine a heat transfer coefficient that is different from the physical properties usually determined by that method.

The above-noted prior art "B" describes the determination of thermal conductivity and kinematic viscosity, which are the physical properties usually determined by that method. However, the specific method described therein is different from the method according to the present invention in that with the present invention fluid temperatures are measured inside and outside of a temperature boundary layer of laminar flow, formed around the heating sensor which is capable of generating heat and measuring its own temperature.

SUMMARY OF THE INVENTION

It is the principal object of the invention to provide a method for the simultaneous determination of thermal conductivity and kinematic viscosity of a fluid utilizing the steady-state method by observing the effect of a temperature boundary layer of laminar flow, formed around a heating sensor capable of generating heat and measuring its own temperature.

The object set forth above is achieved, in accordance with the invention, by a method for simultaneous determination of thermal conductivity and kinematic viscosity of a fluid using a heating sensor capable of generating heat and measuring its own temperature and a thermometric element used to measure the fluid temperature. The method comprising steps of controlling the heating value of the heating sensor so that the thermometric element is positioned inside of a formed temperature boundary layer around the heating sensor after heat generation by the heating sensor, measuring the temperature of the heating sensor as well as the temperature of the fluid and determining the thermal conductivity of the fluid from these measured temperatures. Then the heating value of the heating sensor is controlled so that the thermometric element is positioned outside of the temperature boundary layer thus formed by the further control of the heat generation by the heating sensor. The temperature of the heating sensor and the temperature of the fluid are measured and the kinematic viscosity of the fluid is determined from these measured temperatures.

Within the scope of the invention, two thermometric elements are used, one of which is placed inside the temperature boundary layer formed around the heating sensor and another of which is placed outside the temperature boundary layer. Thus, by controlling the heating value of the heating sensor, values of the two physical properties under the condition of a constant heating value of the heating sensor can be simultaneously determined without the need to shift the position of the temperature boundary layer.

Alternatively, a combination of two heating sensors and a single thermometric element may be used for such temperature measurement of the fluid, wherein the respective heating sensors are immovably placed so that the temperature boundary layers formed around the respective heating sensors do not overlap each other, while the thermometric element is placed inside the temperature boundary layer formed around one of the heating sensors and outside of the temperature boundary layer formed around the another of the heating sensors, so as to simultaneously achieve determination of the two physical properties. Here, it should be understood that, in this embodiment, the values of the physical properties are determined with the heating value of the heating sensor being maintained constant, as in the previously mentioned embodiment.

BRIEF DESCRIPTION OF THE DRAWINGS

The above and other objects of the invention will be seen by reference to the description in connection with the accompanying drawings, in which.

Figure 2:
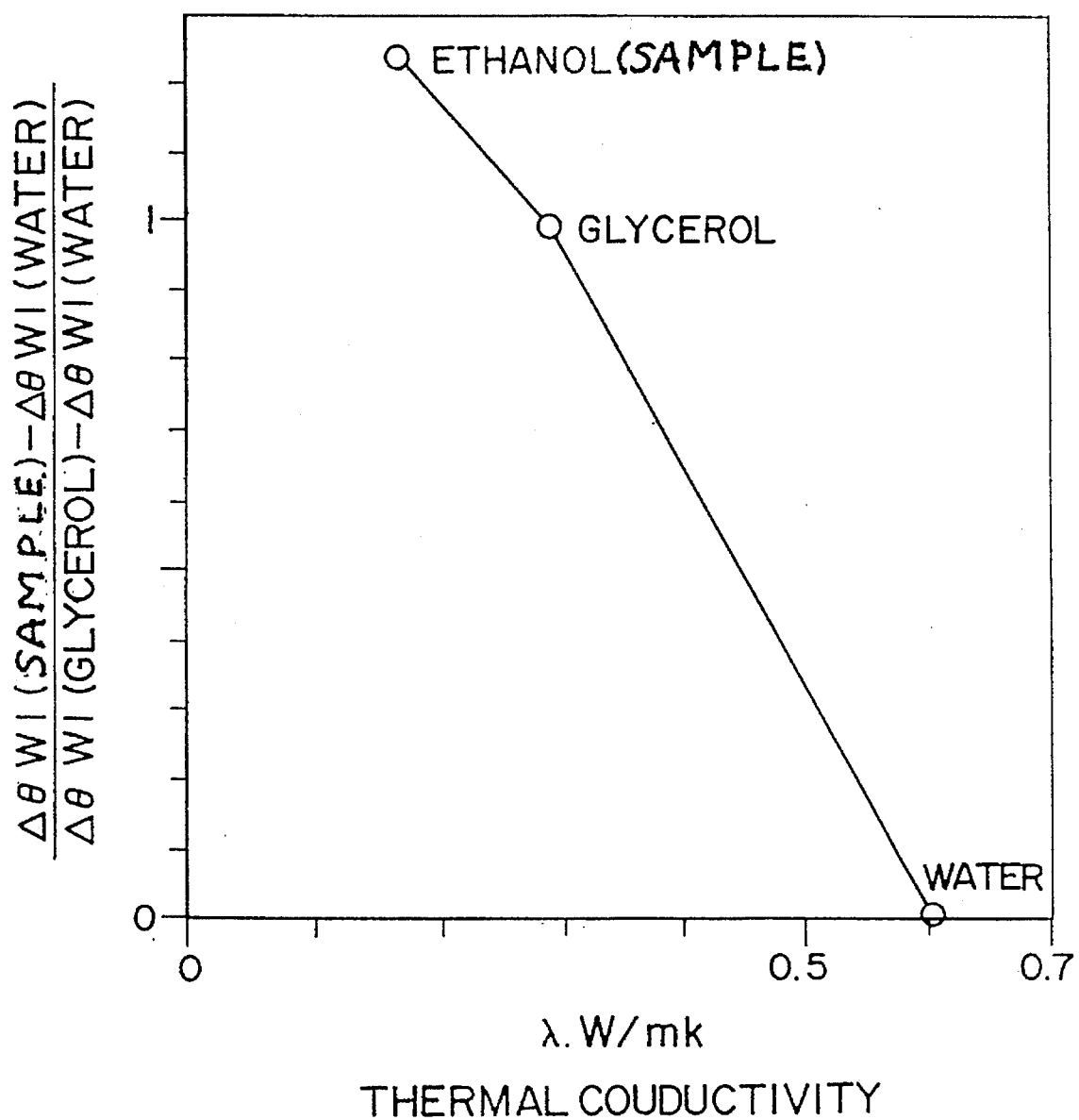
FIG. 2 is a graphic diagram plotting the relationship between thermal conductivity and the characteristic value of {$\Delta\Theta w1$ (sample fluid)–$\Delta\Theta w1$ (pure water)/$\Delta\Theta w1$ (glycerol)–$\Delta\Theta w2$ (pure water)} based on equation (1)
Figure 3:
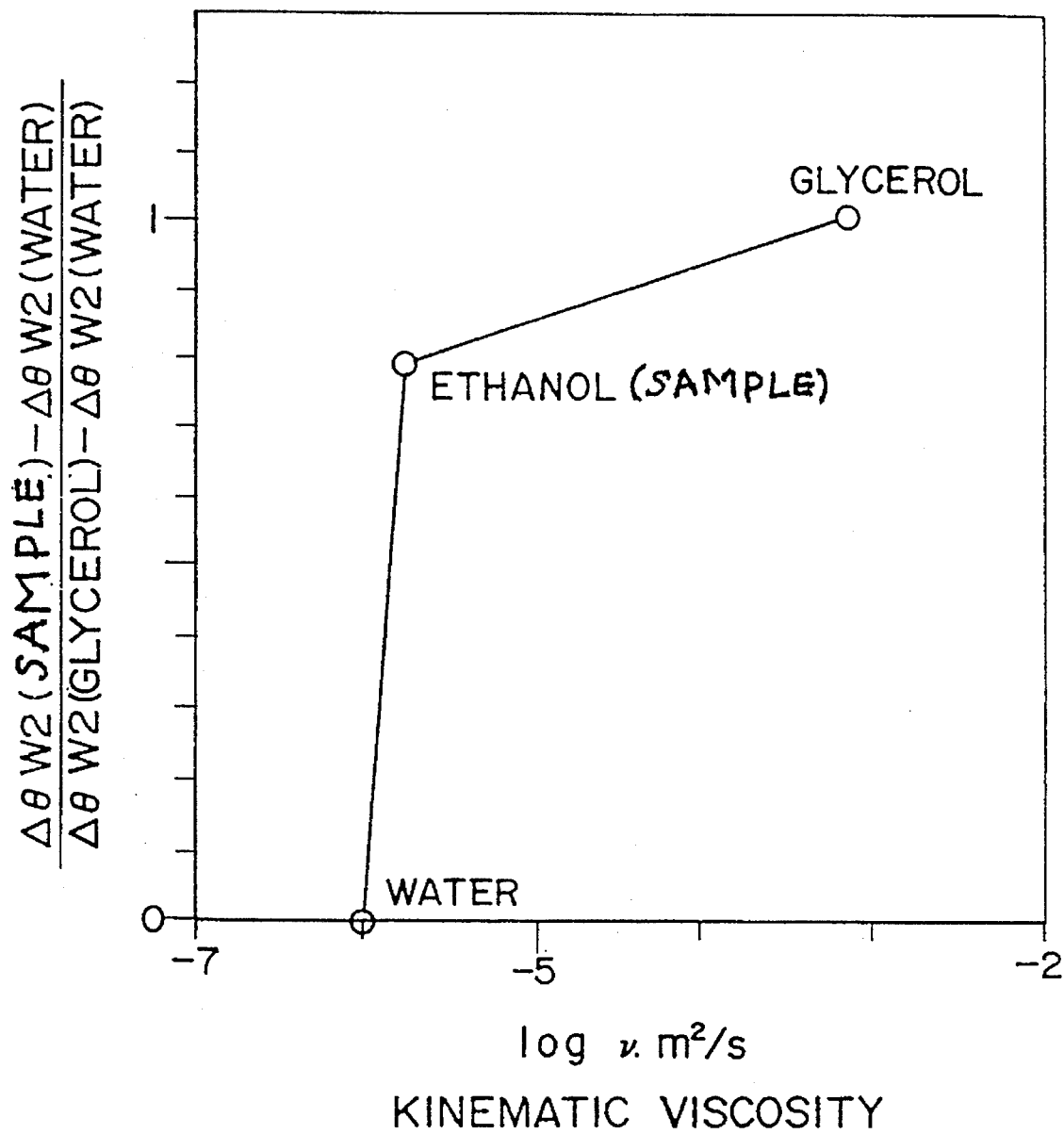
FIG. 3 is a graphic diagram plotting the relationship between the kinematic viscosity and the characteristic value of {$\Delta\Theta w2$ (sample fluid)–$\Delta\Theta w2$ (pure water)/$\Delta\Theta w2$ (glycerol)–$\Delta\Theta w2$ (pure water)} based on equation (1).

$\Delta\Theta w1$ and $\Delta\Theta w2$ in FIGS. 2 and 3 represent the prevailing temperatures of each fluid corresponding to the temperatures of this fluid as measured inside and outside the temperature boundary layer.

DETAILED DESCRIPTION OF THE INVENTION

The invention will be described in reference to embodiments thereof.

Figure 1:
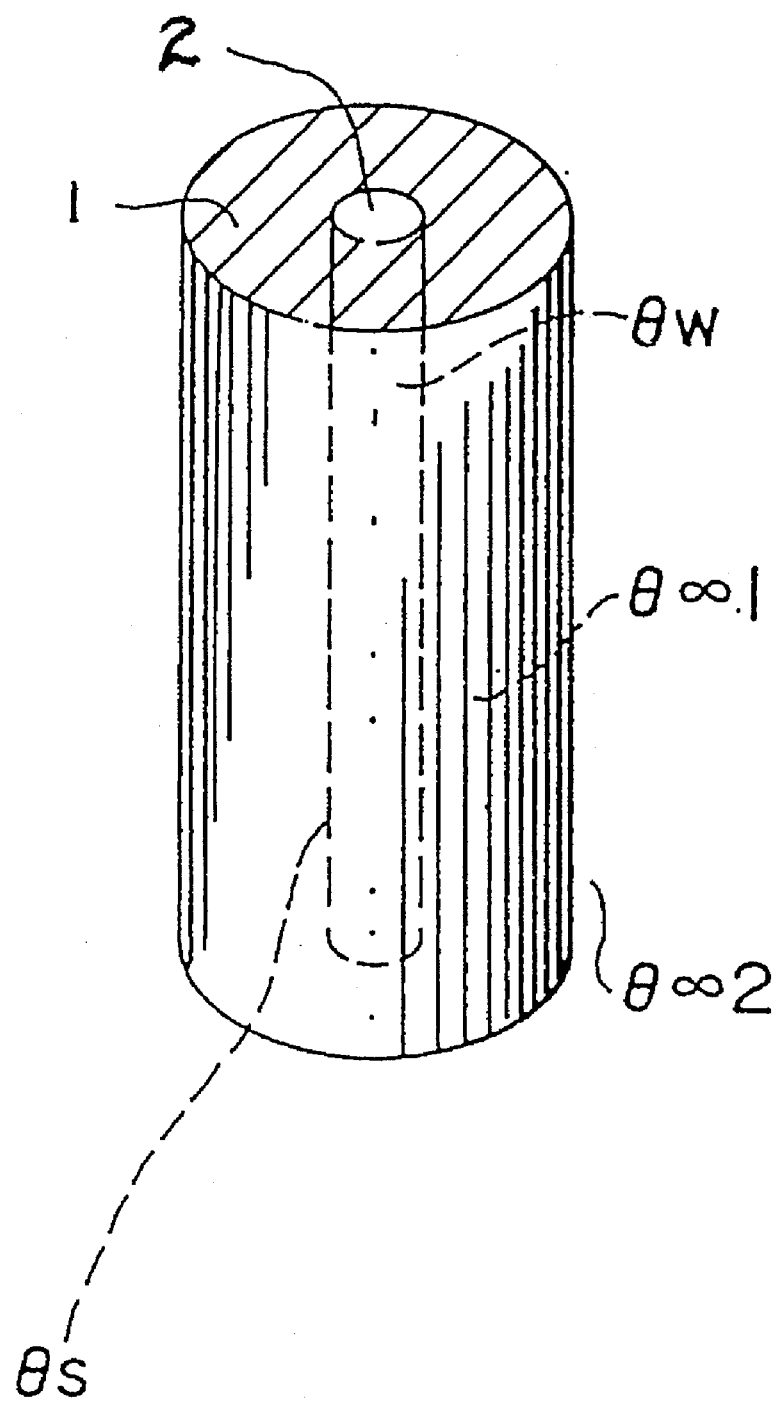
FIG. 1 is a diagram illustrating the temperature boundary layer formed around the heating sensor of the invention.

FIG. 1 of the accompanying drawings illustrates the temperature boundary layer 1 formed around the heating sensor 2 capable of generating heat and measuring its own temperature.

Between the average temperature of the heating sensor $\Theta w$ of the heating sensor and the surface temperature of the heating sensor $\Theta s$ thereof is established a relationship as follows:

$$\Theta w = \Theta s + Co(Q/L)$$

where Q represents the heating value, L represents the length of the sensor and Co represents a constant peculiar to the sensor.

So long as Q is constant, there is established between the changing rate $d\Theta w$ of $\Theta w$ and the changing rate $d\Theta s$ of $\Theta s$ a relationship as follows, even if Co is unknown:

$$d\Theta w = d\Theta s$$

More specifically, a change in $\Theta s$ directly reflecting the fluid state characterized by its thermal conductivity and kinematic viscosity can be represented by a change in $\Theta w$ which can always be measured directly even when Co and/or L and/or Q are unknown. (Ref. Miyawaki, et al: "Fundamental Aspects of Viscosity Monitoring by the Hot Wire Technique", Journal of Food Science, Volume 55, No. 3:854–857 (1990)).

The present invention is characterized in that the steady-state hot wire method, well known as the preferred method for monitoring changes in viscosity of a fluid, is used along with the above-mentioned relationships to simultaneously obtain the thermal conductivity and the kinematic viscosity of a fluid. It is well known that the characteristic differential temperature value defined by the difference between said $\Theta s$ and the temperature of the fluid is actually affected not only by viscosity but also by thermal conductivity. However, a system negligibly affected by thermal conductivity has conventionally been assumed so as to monitor only a change in viscosity. In other words, the conventional characteristic value $\Delta\Theta w = \Theta w - \Theta\infty$ has always assumed the temperature of the fluid measured at 10 an infinitely remote point as the prevailing temperature of this fluid.

According to the present invention, on the other hand, the prevailing temperature of the fluid is defined by two temperatures, i.e. the temperature as measured at an infinitely remote point and the temperature of the fluid as measured inside a temperature boundary layer $\Theta\infty 1$ (see FIG. 1) formed around the heating sensor. Therefore, correspondingly, two characteristic differential temperature values are obtained so that the thermal conductivity is determined on the basis of the characteristic differential temperature value derived from the temperature of the fluid as measured inside the temperature boundary layer $\Theta\infty 1$, and the kinematic viscosity is determined on the basis of the characteristic differential temperature value derived from the temperature of the fluid as measured outside the temperature boundary layer $\Theta\infty 2$ (see FIG. 1).

The operation of the present invention will now be described. As noted above, the simultaneous determination of thermal conductivity and kinematic viscosity of a fluid is achieved, according to the invention, by obtaining the temperature of the heating sensor, or the difference between this temperature and the temperature of the fluid, as a characteristic value and utilizing a correlation between that characteristic value and respective physical properties. In this regard, it is well known to use merely the temperature of the fluid and the temperature of the heating sensor, or the difference therebetween. Compared to such prior art, a remarkable novelty of the present invention lies in that the prevailing temperature of the fluid is considered in relation to a temperature boundary layer 1 (see FIG. 1) of laminar flow formed around the heating sensor and the heating value of the heating sensor is defined by the thickness of that temperature boundary layer. A plurality of such heating values are preset so that the temperatures of the fluid may be measured inside and outside the boundary layer, $\Theta\infty 1$ and $\Theta\infty 2$, with a single thermometric sensor immovably placed to measure the temperature of the fluid and the preset values, or with a plurality of such thermometric sensors placed inside and outside the boundary layer under a constant heating value. These measurements may be used to determine thermal conductivity and kinematic viscosity simultaneously.

Alternatively, the temperatures of two heating sensors, placed in two reference fluids or differences between these temperatures and temperatures of the respective references fluids, may be measured inside and outside temperature boundary layers formed around the heating sensor. These temperatures are then used to obtain the characteristic value. By this method, the results are free from any affect due to particular construction of the heating sensor or any affect due to fluctuation in the heating value of the heating sensor. Correlations between the so-obtained characteristic value and the respective physical properties is used to determine desired physical properties in a more accurate manner.

It should be understood that the characteristic differential temperature value $\Delta\Theta$ is defined by the following equation which is based on the differences between (a) the temperature of the heating sensor placed in the fluid and two temperatures of the fluid defined by the two prevailing temperatures, or (b) the differences between the temperature of the heating sensor placed in reference fluids at a normal state and the temperatures of the respective reference fluids, which later method is a preferred embodiment, as illustrated by the Example:

$$\text{Characteristic value } (\Delta\Theta) = (C-A)/(B-A) \quad (1)$$

where A, B and C represent characteristic differential temperature values (i.e. temperature of the heating sensor—prevailing temperatures of the respective fluids), respectively, obtained with respect to the reference fluids 1, 2 and the fluid to be monitored.

The prevailing temperatures of the respective fluids may be measured by providing a heating sensor having the same construction as the heating sensor, but activated only in regard to its thermometric function, while controlling the electric current to be applied thereto, or by separately providing ordinary thermometric elements.

The respective characteristic values are defined by the differential values between the temperature of the heating sensor and the temperatures of the respective fluids, as measured inside and outside the temperature boundary layer of laminar flow formed around the heating sensor. The thermal conductivity and the kinematic viscosity reflected by the respective characteristic values can be simultaneously determined, so the present invention is effectively applicable to process management for handling fluids of general types presenting simultaneous changes in thermal conductivity and kinematic viscosity, thus making real time process control possible.

EXAMPLE

This example describes using the above-mentioned characteristic differential temperature value, generalized by the equation (1), with water and glycerol as the two different reference fluids.

FIG. 2 plots a relationship established between the characteristic value, as defined by equation (1), and the thermal conductivity of the fluid to be monitored. The characteristic value is a function of the difference between the temperatures of a heating sensor and the temperature of the fluid. A conventional heating sensor capable of measuring its own temperature and having a diameter of 0.6 mm, a length of 4 mm, and a heating value of 0.02 watt was placed in the respective fluids, i.e. water, ethanol (the "Sample Fluid" and glycerol, at standard conditions (i.e. normal pressure, 30° C). The temperature of the sample fluid to be monitored was measured inside the temperature boundary layer of laminar flow (at a distance of 1 mm from the heating sensor) with conventional temperature readouts.

FIG. 3 plots a relationship established between the determined characteristic value and kinematic viscosity of the fluids of FIG. 2, wherein the temperature, as measured outside the temperature boundary layer of laminar flow, is used as the temperature of the fluid (at a distance of 20 mm from the heating sensor).

As is well known, concerning kinematic viscosity, glycerol>ethanol>water and, concerning thermal conductivity, water>glycerol>ethanol. It will be apparent from FIGS. 2 and 3 that all the characteristic values are in accordance with the orders as indicated above. This example, thus, verifies that a correlation is established between the characteristic value defined in accordance with the invention and the thermal conductivity, and similarly, a correlation is established between said characteristic value and kinematic viscosity of the fluid.

It is also possible that the temperature of the heating sensor and the temperatures of the fluid, as measured inside and outside the temperature boundary layer of laminar flow formed by this fluid around the heating sensor, are measured, and therefrom thermal conductivity and kinematic viscosity of this fluid are simultaneously determined utilizing FIGS. 2 and 3.

While the invention has been particularly shown and described with reference to preferred embodiments thereof, it will be understood by those skilled in the art that the foregoing and other changes in form and details can be made therein without departing from the spirit and scope of the invention.

What is claimed is:

1. Method for determination of thermal conductivity and kinematic viscosity of a fluid, comprising:

(1) placing a heating sensor capable of generating heat and measuring its own temperature in the fluid;

(2) placing a thermometric element capable of measuring the fluid temperature in the fluid;

(3) heating the heating sensor and controlling the heating value thereof so that the thermometric element is positioned inside a first temperature boundary layer formed around the heating sensor;

(4) measuring a first temperature of the heating sensor;

(5) measuring a first temperature of the fluid;

determining thermal conductivity of the fluid from said measured first temperatures of the heating sensor and fluid;

(6) controlling the heating value of the heating sensor so that the boundary layer is changed such that the thermometric element is positioned outside the changed temperature boundary layer;

(7) measuring a second temperature of the heating sensor;

(8) measuring a second temperature of the fluid; and determining kinematic viscosity of the fluid from said measured second temperatures of the heating sensor and fluid.

2. The method of claim 1, wherein the thermometric element is a heating sensor adapted to function as a thermometric element by control of electric current thereto.

3. The method of claim 1, wherein the thermometric element is a dedicated thermometric element.

* * * * *